United States Patent [19]

Brenman et al.

[11] Patent Number: 4,590,942

[45] Date of Patent: May 27, 1986

[54] APPARATUS AND METHOD FOR INHIBITING NASAL SECRETIONS

[75] Inventors: Henry S. Brenman, Cinnaminson, N.J.; Harold L. Schwartz, King of Prussia, Pa.; Philip Katz, Princeton Junction, N.J.

[73] Assignee: Biosonics, Inc., Phila., Pa.

[21] Appl. No.: 581,061

[22] Filed: Feb. 17, 1984

[51] Int. Cl.[4] .................................................. A61N 1/36
[52] U.S. Cl. .................................. 128/419 R; 128/787
[58] Field of Search ...... 604/20; 128/419 R, 421–423, 128/741, 787

[56] References Cited

U.S. PATENT DOCUMENTS

| | | | |
|---|---|---|---|
| 1,943,543 | 1/1934 | McFadden | 128/787 |
| 2,532,788 | 12/1950 | Sarnoff | 128/419 G |
| 3,461,874 | 8/1969 | Martinez | 128/303.17 |
| 3,773,051 | 11/1973 | Holcomb et al. | 128/422 |
| 3,902,502 | 9/1975 | Liss et al. | 128/422 |
| 4,033,356 | 7/1977 | Hara | 128/422 |
| 4,102,348 | 7/1978 | Hihara et al. | 128/422 |
| 4,177,819 | 12/1979 | Kofsky et al. | 128/422 |
| 4,392,496 | 7/1983 | Stanton | 128/423 W |

FOREIGN PATENT DOCUMENTS 912172  3/1982  U.S.S.R. ......................... 128/419 R

Primary Examiner—William E. Kamm
Assistant Examiner—Mitchell J. Shein
Attorney, Agent, or Firm—Robert C. Podwil

[57] ABSTRACT

Apparatus for inhibiting nasal secretions by selective neural stimulation applies an electrical signal to a selected neurally sensitive area of the oral cavity. A method for inhibiting nasal secretions includes the steps of applying an electrical signal to a neurally sensitive area in the oral cavity, such as on opposite sides of the frenulum and beneath the philtrum.

14 Claims, 8 Drawing Figures

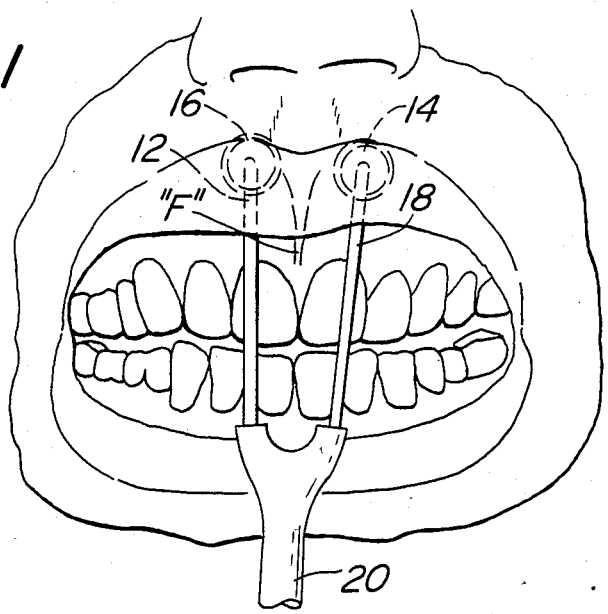
FIG. 1
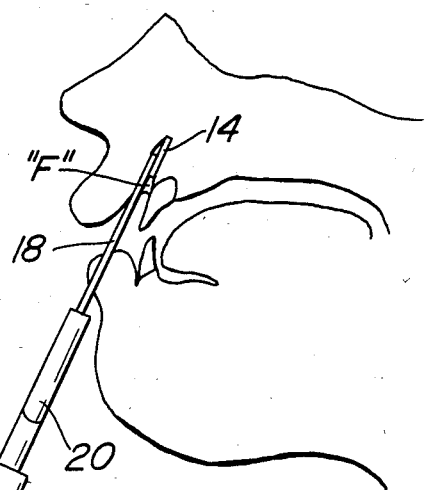
FIG. 2
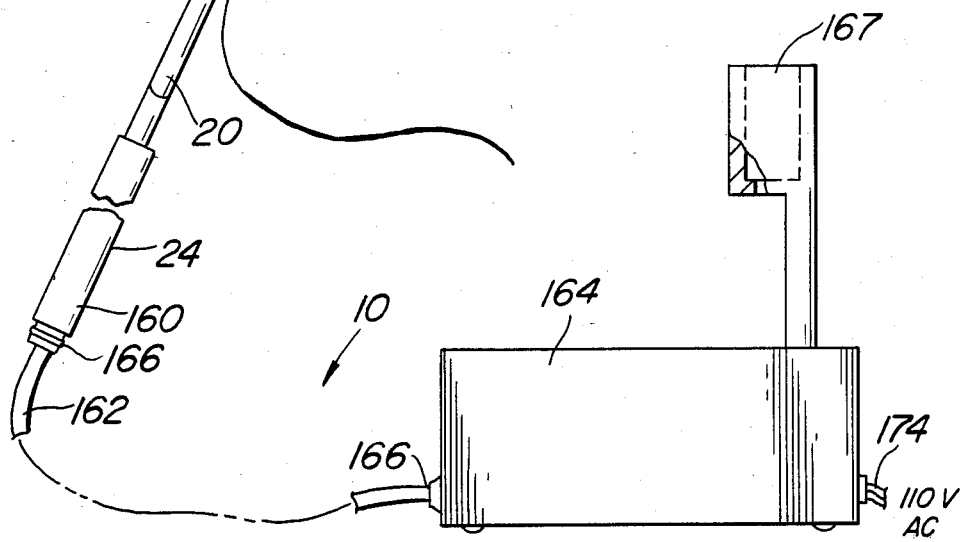

APPARATUS AND METHOD FOR INHIBITING NASAL SECRETIONS

BACKGROUND OF THE INVENTION

This invention relates to apparatus and a method for inhibiting nasal secretions, and more particularly, to apparatus and a method for inhibiting nasal secretions by the application, intra-orally, of electrical energy to nerves affecting the nasal sinus area. Such stimulation, it has been found, can temporarily modify the nasal sinus area so as to reduce the acute effects of pollen and other allergens, and potentially to reduce post-nasal drip. In its apparatus aspect, the present invention relates to a device that contains stimulating electronics and an appropriate power supply, and a pair of electrodes capable of passing stimulating energy across the frenulum that exists beneath the upper lip and between the front teeth.

The application of an appropriate signal in this particular location has been found in preliminary studies to produce temporary, but still relatively long-lasting effects, on the nasal sinus area.

In the method aspect of the invention, a signal which has been found to be efficacious is applied at a particular location, to produce the desired results.

The electrode placement, it has been found, is quite crucial, in that the application of a stimulating signal to the tooth side of the gums can produce unpleasant sensations (similar in their effect to cold sensitivity) in the upper front teeth.

In the performance of the present invention, patients are first tested for suitability as subjects for the method. This is accomplished by applying to the potential subject, in the critical area, an electrical signal which simulates the signal to be produced by the apparatus. If the desired response is obtained, further testing is used to establish a minimum effective dosage level (duration and voltage level) for that individual. An apparatus can then be tailored to that individual's responsiveness and susceptibility. Apparatus in accordance with the present invention need not, however, necessarily be custom-fitted for each subject. Rather, a generalized shape, capable of applying the necessary signal to the above-described areas, will suffice.

It has been found efficacious, in accordance with the present invention to apply a signal of three minutes duration. Although present clincial tests are not definitive, it is thought that the frequency of required application may be in a range of from daily to every three to five days, depending upon the patient and the severity of the patient's condition.

Accordingly, it is a principal object of this invention to provide an apparatus and a method for inhibiting nasal secretions, which is both compact, reliable and simple to use. Another object of this invention is to provide a method for inhibiting nasal secretions by means of electrical stimulation.

Other objects will appear hereinafter.

It has heretofore been proposed that electrical energy be applied in the oral cavity for a variety of medical reasons, but not for the purpose nor in the manner described herein. For example, in Russian Pat. No. 721,109, issued Aug. 15, 1977, a method is disclosed for treating inflammation of salivary glands by filling the salivary ducts with a liquid medication under pressure, and then using the liquid to carry out electrophoresis.

In German Offenlegungschrift No. 2740-188, published Mar. 8, 1979, a technique is disclosed for the application of an electrical stimulus to the gums to prevent, so the publication states, atrophy or bleeding of the gums and decay of the teeth.

In U.S. patent application Ser. No. 06/481,331, filed Apr. 1, 1983, and assigned to the assignee of the present invention, it was disclosed that salivation may be induced by applying electrical stimulus to certain areas of the hard palate.

SUMMARY OF THE INVENTION

The above and other objects are realized, in a presently preferred form of the invention, by apparatus, preferably hand-held, which supplies a pair of electrodes capable of passing stimulating energy across the frenulum that exists between the upper front teeth. Electrical signal generating means are electrically coupled to the electrodes, and the electrodes can be selectively placed in a neurally sensitive area of the oral cavity (such as the area adjacent to the frenulum and below the philtrum) when the apparatus is operatively disposed. Identification of neurally sensitive areas may be accomplished by applying to the oral cavity, on an exploratory basis, an electrical signal which simulates the inhibiting signal produced by the signal generator. This may be accomplished through the use of glove-mounted electrodes of the kinds described in U.S. patent application Ser. No. 06/452,319, filed Dec. 22, 1982, for "Means for Transferring Electrical Signals to and From Living Tissue" (assigned to the Assignee of the present application), or other suitable means. It is contemplated that a clinician or laboratory or hospital facility might have a device of a generalized type, suitable for use in evaluating potential users of the apparatus. Using such a device, the effective dosage level for the individual may be established, and the individual may then be provided with a custom-fitted device for his or her personal use. Use of the above-described diagnostic or exploratory technique can identify candidates for use of the present apparatus and method. Evaluation in the above-described manner identifies a neurally sensitive "target" area to which apparatus in accordance with this invention may apply an inhibiting signal. It may also identify the "dosage" suitable for a given subject, and screen out those for whom the apparatus and method is not likely to be helpful.

In its method aspect, the present invention involves the technique of inhibiting nasal secretions by the steps of locating and stimulating the nerves of the oral cavity of a user to identify areas which are sensitive to neural stimulation by electrical means, then placing in the oral cavity of the user, on opposite sides of the frenulum and beneath the philtrum, a pair of electrodes, and generating and applying to the electrodes a stimulating signal, preferably on the order of about six volts and of a particular pulse width and frequency.

There is seen in the drawings a form of the invention which is presently preferred (and which represents the best mode contemplated for carrying the invention into effect), but it should be understood that the invention is not limited to the precise arrangements and instrumentalities shown or described.

DESCRIPTION OF DRAWINGS

FIG. 1 is a frontal pictorial view, partly cut away, showing an embodiment of the apparatus in accordance with the invention operatively disposed with respect to the lips and gums of a user.

FIG. 2 is another view, similar to FIG. 1, showing the manner in which electrodes of the present apparatus may be positioned and used.

DETAILED DESCRIPTION

Figure 3:
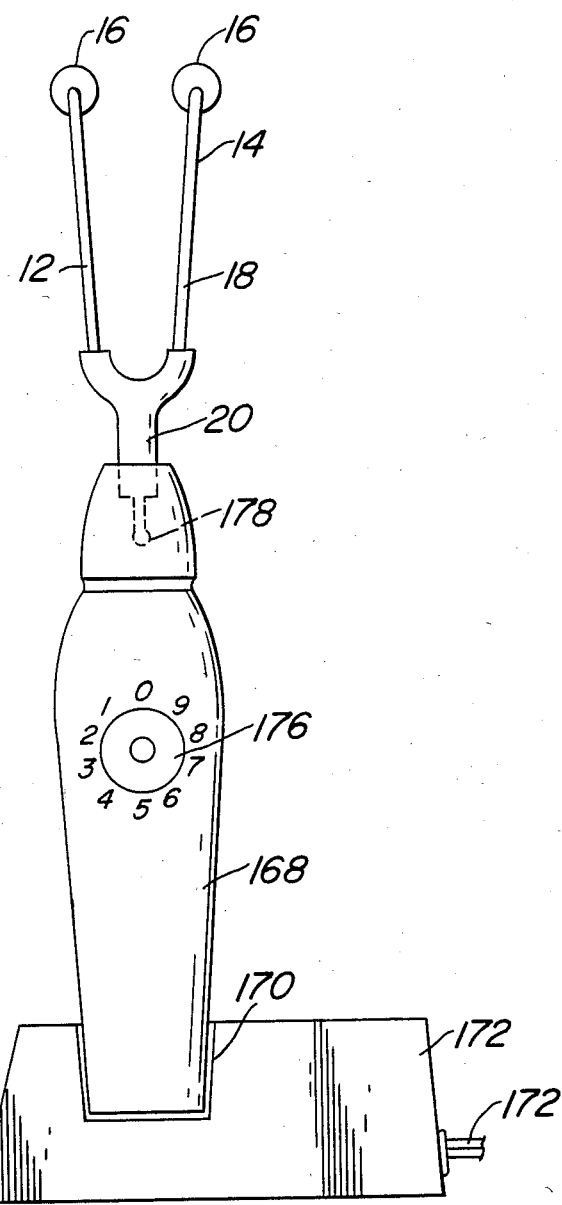
FIG. 3 is a pictorial view, showing apparatus in accordance with the invention, including a base, a hand-held housing and electrodes associated with the housing.

Referring now to the drawings in detail, wherein like reference numerals indicate like elements, there is seen in FIGS. 1 to 3 apparatus designated generally by the reference numeral 10, for inhibiting nasal secretions by selective neural stimulation.

As is seen in FIGS. 1 to 3, the apparatus 10 comprises a pair of electrodes 12 and 14, which may be introduced into the oral cavity of the user in a manner to be described below. The electrodes 12 and 14 are, respectively, active and ground, or passive, electrodes so that an electrical potential applied to the electrode 12 may, when both electrodes are placed in contact with the mocosa of the oral cavity and in close proximity to each other, form an electrical circut.

As is perhaps best seen in FIG. 3, the electrodes 12 and 14 are provided with enlarged ends 16 which enhance surface contact between the electrodes 12 and 14 and the mucosa.

The enlarged ends 16 are preferably affixed to resilient or adjustable mounting rods 18, and oriented with respect to the mounting rods 18 so as to facilitate insertion of the electrodes into the narrow space between the upper lip and the gum. The mounting rods 18 for the electrodes 12 and 14 are advantageously anchored in a unitary support structure 20, which, in turn, may be associated with a hand-held support 24, 24' as later described.

Figure 5:
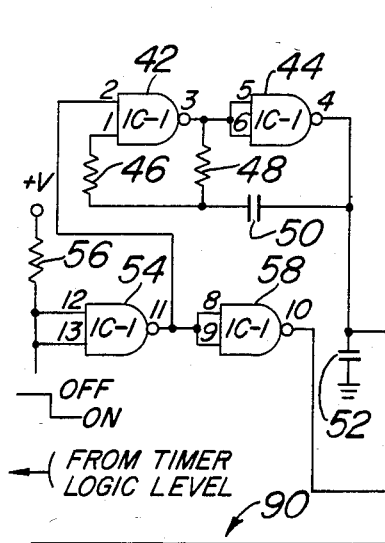
FIG. 5 is a schematic circuit diagram illustrating exemplary electronic circuit means for generating a stimulating signal for use in the present invention.

FIG. 5 illustrates presently preferred electronic circuitry for the pulse generator 40 of the apparatus 10, utilizing microminiature components in the "LIDS" or "DICE" size packages, although any standard CMOS equivalent integrated circuitry could also be used. Gates 42, 44, 46 and 48 are four quarters of a quad, two-input NAND integrated circuit (LIDS LFG 4011 or equivalent), also referred to collectively as IC-1. Such devices are sold by Amperex Electronics Corporation, a subsidiary of North American Phillips Corp. as so-called "leadless inverted devices" (hence, "LIDS"). Such devices are electronically equivalent to conventional integrated circuits of the CMOS 4011 type, available from manufacturers such as, among othrs, RCA, Texas Instrument Corp., National Semiconductor Corp. and Solid State Scientific Corp.

It is preferred that the pulse generator 40 be designed to produce a peak output of approximately 2.4 mA, which is calculated on the basis of an assumed output voltage of about 6 volts into an impedance of about 2500 ohms, and it will produce a constant output current regardless of the impedance fluctuations across the mucosa of the user. Such fluctuations can be considerable due to the fact that the medium surrounding the electrodes 12 and 14 will vary considerably in wetness, with substantial impedance changes between the two conditions. A current-limited configuration, as is presently preferred, has been found to avoid the high current spikes which might occur in low impedance conditions, and it also conserves battery power.

The electrodes 12 and 14 are electrically coupled to a signal generating means, which will now be described in detail.

Figure 7:
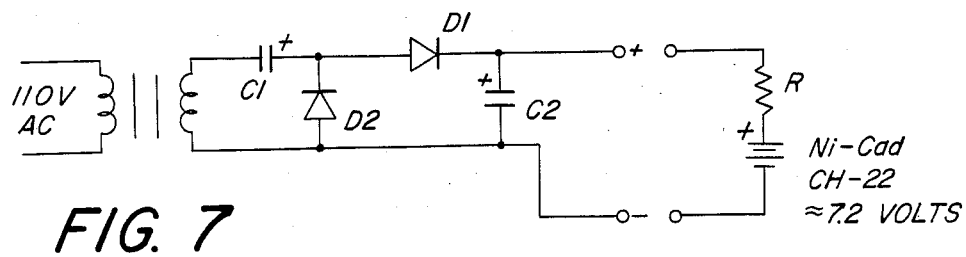
FIG. 7 is a schematic circuit design of an exemplary doubler circuit for use in the present invention.
Figure 4:
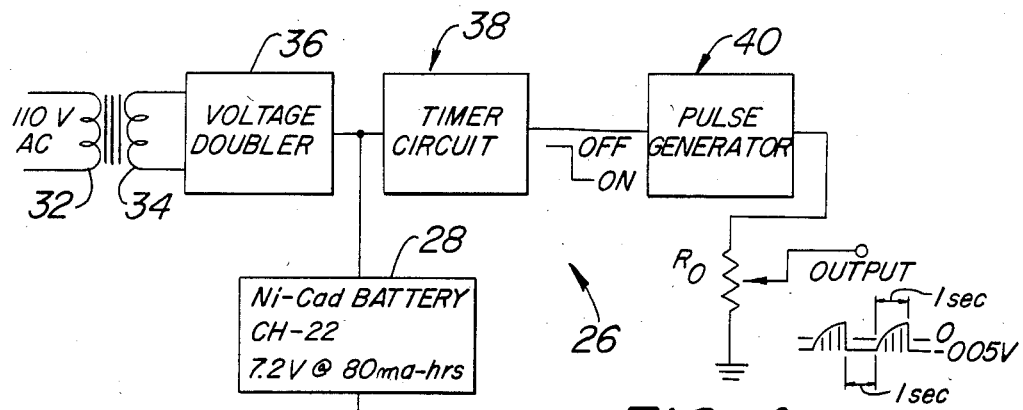
FIG. 4 is a block diagram of the circuitry of apparatus in accordance with the invention.

Referring now to FIG. 4, there is seen a block diagram for the signal generating means, designated generally by the reference numeral 26. In general, the signal generating means 26 includes a highly miniaturized and self-contained pulse generator with associated power supply, timing and control circuitry. Thus, referring to FIG. 4, a power supply 28 is provided, which, in the illustrated embodiment includes nickel cadmium batteries (CH-22 or equivalent) of a nominal nine-volt rating, but which provide 7.2 volts at 80 milliampere-hours. The power supply 28 is rechargeable from a 110-volt A.C. source, applied to the primary winding 32 of a transformer. The secondary winding 34 of the transformer is applied to a voltage doubler circuit 36, itself illustrated in FIG. 7. The voltage doubler circuit is of conventional configuration and may be easily modified for higher voltages.

The power supply 28 feeds a timer circuit designated generally by the reference numeral 38, and the output of the timer circuit 38 controls the operation of a pulse generator, designated generally by the reference numeral 40. The pulse generator 40 produces across a variable output resistor $R_0$ a biphasic output signal which can be applied to the electrodes 12 and 14 (which are not seen in FIG. 4).

The gates 42 and 44, together with their passive components, the resistors 46, 48 and the capacitor 50 make up an astable multivibrator, whose output frequency is approximately 525 Hz, T equals 1.9 milliseconds. The values of resistors 46 and 48 and capacitor 50, in such an arrangement can be 2.2 Mohms, 100 kohms and 0.01 $\mu$F, respectively. The ground capacitor 52 may have a value of 120 pF.

The astable multivibrator 42, 44 may itself be gated by the action of a switch (not shown) or preferably by the electronic equivalent of such a switch, the time logic level applied at its pin 2, from gate 54 pins 11, 12 and 13 of IC-1.

Gate 54 is enabled by the timer circuit 38, described below, and powered by the output of the power supply 28, applied through a load resistor 56 of 1 Mohms. The output of gate 54 is also applied to gate 58, pins 8, 9 and 10, of IC-1, and after inversion by gate 58 is applied as a low voltage reference to a binary counter 60 (also referred to as IC-3). The output of the astable multivibrator, gates 42 and 44, is also applied as a clock input to the binary counter 60 (IC-30). The output (at $Q_4$), pin 7, of the binary counter 60 is a 30 millisecond square wave, which acts as an input to a monostable multivibrator comprising gates 62 and 64 (pins 8, 9, 10 and 11, 12 and 13) of IC-2, another quad, 2-input NAND integrated circuit of the same type as IC-1. The passive components associated with the gates of 62 and 64 may, advantageously, have the following values: the resistor 66, 33 kohms; the resistor 68, 33 kohms; and the capacitor 70, 0.01 μF. A capacitor 72 is disposed between the output $Q_4$ of the binary counter 60 and the feedback loop of the monostable multivibrator provided by gates 62 and 64. It, too, advantageously, has a value of 0.01 μF.

The output of the monostable multivibrator comprising gates 62 and 64 is a 0.5 millisecond pulse, every 30 milliseconds. This signal, taken from pin 10 of IC-2, schematically between the output of the gate 62 and the capacitor 70, is applied to a gate 74 (pin 12) of IC-2. Also applied to the gate 74 (at pin 13 of IC-2) is the output $Q_{10}$ (pin 14) of the binary counter 60. This output is a 2 second square wave (second high-second low). The output of gate 74 is a series of square pulses of 0.5 milliseconds duration every 30 milliseconds, for a period of 1 second, and then off for 1 second. This signal is inverted by a gate 76, and is seen as an output at pin 10 of IC-2.

The above-described output applied through a resistor 78 provides the collector drive voltage of a transistor stage 80, and it turns stage 80 on and off at the above-described frequency, the stage 80 being on only when the individual pulses are high ("1") during the 1 second interval. This aspect of the circuitry enables the pulse generator 40 to provide a gated power supply which is locked in at the desired frequency and which reduces power supply drain.

The output signal for the pulse generator 40 is provided by the output of the binary counter 60 stages $Q_{4-9}$ (at pins 7–13 of IC-3), through load resistors 82(a)–(e). The outputs of the counter stages are summed and applied to the base of the transistor element 80. Gating, as described above, of the collector signal of the transistor element 80 yields a collective waveform at the emitter of the transistor element 80 which is a staircase made up of individual pulses of about 0.5 msec. in width, rising incrementally for one second, followed by a one second "off" period, and then another staircase-form collective signal of one second width.

In the form of the apparatus illustrated in FIG. 5, the load resistors 82(a)–(e) have values, respectively, of 470 kohms, 220 kohms, 100 kohms, 51 kohms and 27 kohms.

Figure 5A:
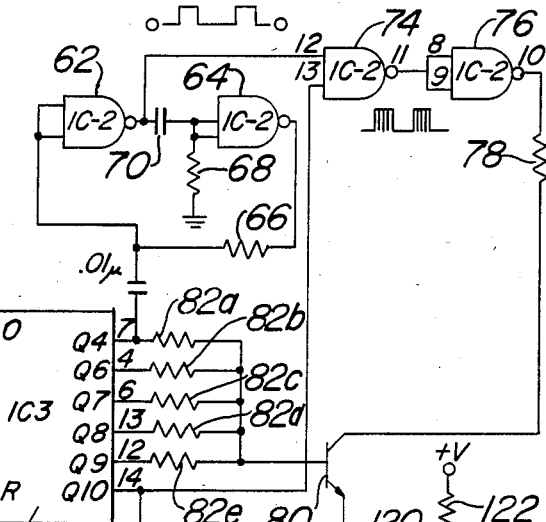
FIG. 5a is a variation of a portion of the schematic circuit diagram shown in FIG. 5.

The emitter resistor associated with the transistor stage 80 may be either a 25 kohm potentiometer 84 as shown in FIG. 5, or, as illustrated in FIG. 5a, a resistor divider network made up of resistors 86 and 88. The potentiometer 84 or, as the case may be, resistor divider, provides an amplitude control for the output signal.

Referring to FIG. 5, there is seen circuitry designated generally by the reference numeral 90, which provides a negative voltage which, with appropriate phasing with respect to the positive signal provided by other circuitry, enables the pulse generator 40 to provide a biphasic output with a net D.C. equal to zero.

Referring again to FIG. 5, the voltage signal at pin 10 of the binary counter 60, as manifested in conductor 92, is applied to a differentiator, consisting of a capacitor 94 and resistor 96. The voltage signal at pin 10 of the binary counter 60 provides a negative excursion which is an exponentially decreasing (from-9 v.) wave form. This signal is rectified and filtered by a diode 98 and capacitor 100. The resulting negative voltage signal is reduced to approximately $-50$ mvolts ($-0.05$ v) by a resistor 102, diode 104 and potentiometer 106, and the output of the potentiometer 106 is applied to an analog switch 108 (LIDS LFS 4016 or equivalent, also referred to as IC-4), through a conductor 110.

A conductor 112, connected to the output $Q_{10}$, pin 14, of the binary counter 60 (IC-3) supplies a control signal for the analog switch 108, in the following manner. The above-described two-second square wave apparent at $Q_{10}$, pin 14, is inverted by the network consisting of a resistor 114, transistor stage 116, and resistor 118, and applied to pin 13 of the analog switch 108, IC-4. When this signal is positive, it enables the analog switch 108, and allows the $-50$ mvolt signal to be presented to the emitter of a transistor stage 120.

In the above described circuitry, the phasing as between the positive and negative voltage outputs is such that during the one second "off time" of the positive voltage output, a negative potential exists to make the net D.C. per cycle equal zero. This is depicted graphically in FIG. 4, wherein the positive voltage output is "on" for one second, and the negative potential of $-50$ mvolt is "on" for one second when the positive voltage output is "off".

The transistor stage 120 provides a current amplifier, with current limiting in the collector of 40 milliamperes instantaneous when resistor 122 has a value of 150 ohms and limiting of 20 milliamperes when the resistor 122 has a value of 330 ohms.

Battery current is approximately 350 microamperes (μA) average, and varies from 260 to 450 μA during the pulse transition times. The following are exemplary values for the above-described circuit elements: capacitor 94, 0.01 μF; resistor 96, 10 kohms; capacitor 100, 1.5 μF; resistor 102, 10 kohms; potentiometer 196; 5 kohms; resistor 114, 100 kohms; and resistor 118, 100 kohms. The diodes 98 and 104 may be IN914 or equivalent.

The following are exemplary values of the resistors 86 and 88 for desired output amplitudes:

| Resistor 82 kohms | | Output |
|---|---|---|
| Vcc = 9 v | Resistor 122 = 150 ohms | |
| | Resistor 84 ohms | |
| 0 | 22 | 6 + volts |
| 3 | 20 | 6.0 |
| | Register 82 kohms | |
| 4.7 | 18 | 5.0 |
| 8.2 | 15 | 4.0 |
| 12 | 10 | 3.0 |
| 15 | 8.2 | 2.0 |
| 18 | 4.7 | 1.0 |
| Vcc = 6 v | | |
| 0 | 22 | 4.0 v |
| 4.7 | 18 | 3.0 v |
| 12 | 12 | 2.0 v |
| 18 | 6.2 | 1.0 v |
| | Resistor 122 = 330 ohms | |
| 0 | 22 | 3.5 v |
| 3.3 | 18 | 3.0 v |
| 8.3 | 15 | 2.5 v |
| 10 | 12 | 2.0 v |
| 15 | 8.2 | 1.0 v |

The above-described circuitry operates to provide the desired net D.C. output equal to zero. In so doing, the variation of its negative and positive output amplitudes is as follows:

| Positive excursion | Negative exercusion |
|---|---|
| (+) 6 v. | (−) 50 mv. |
| 5 | 43 |
| 4 | 34 |
| 3 | 25 |
| 2 | 17 |

-continued

| Positive excursion | Negative exercusion |
|---|---|
| 1 | 9 |

In the above-described circuitry, the binary counter 60 (IC-3), may advantageously be Amperex LIDS LFC 4020 and the analog switch 108 (IC-4), LFS 4061. The transistor elements 84, 116 and 120 may be Amperex LIDS LDA 405 or equivalent. The resistors are IMS-3-2, of the values given above.

Figure 6:
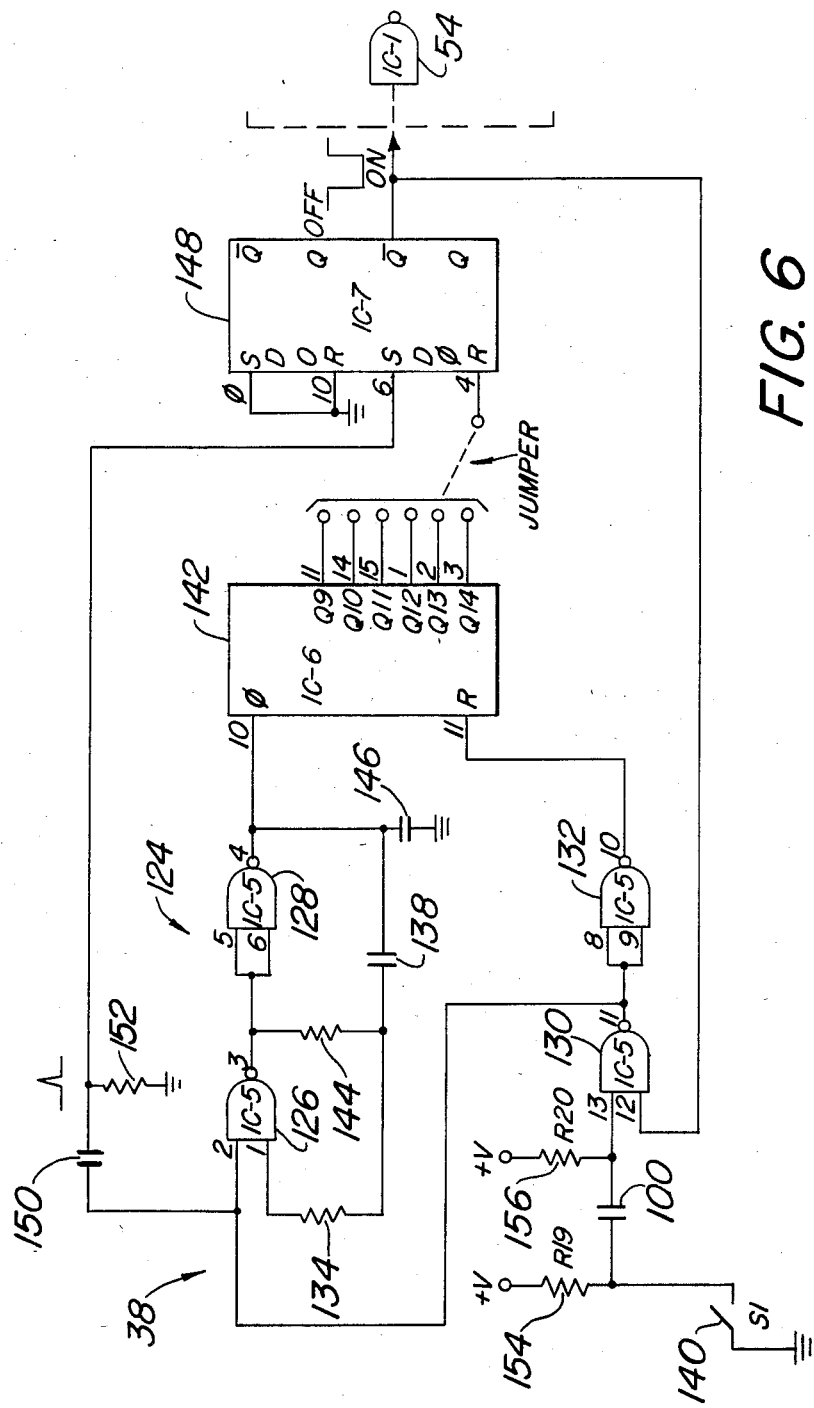
FIG. 6 is a schematic circuit diagram illustrating exemplary timing circuit means for use in the present invention.

Referring now to FIG. 6, the operation of the timer in relation to the pulse generator 40 is as follows. A quad 2-input NAND, designated generally by the reference numeral 124, and sometimes referred to as IC-5, provides gates 126, 128, 130 and 132, gates 126 and 128 of which provide an astable multivibrator with a period of approximately 21 milliseconds. Such a period may be obtained, in the illustrated circuit, by providing the passive circuit elements, resistors 134 and 136, and capacitor 138, associated with the gates 126 and 128, with values of 2.2 Mohms, 51 kohms and 0.15 µF respectively. The astable multivibrator is enabled by closing of a switch 140, which permits a triggering signal, apparent at pin 11 of the gate 130, to be seen at pin 2 of the gate 126.

A counter 142 (IC-6) is driven by the above-described 21 millisecond "clock", with each output of the counter 142 ($Q_1$ (not shown)–$Q_{14}$) acting as a "divide by 2" stage. Thus, the output of $Q_1$ (not shown) would be 42 milliseconds; of $Q_2$ (not shown) 84 milliseconds, etc. After inversion by the gate 132, the output signal of the gate 130 (at pin 11) is applied to the counter 142 as a low voltage (0) reference.

A timing table, illustrating the output times for various configurations of the counter 142 (IC-6) at a clock frequency (determined by the values of the resistor 136 and the capacitor 138) of approximately 21 milliseconds is as follows:

| Timing Table | | |
|---|---|---|
| Reference Q (clock) | Pin No | Output time (sec.) |
| Q1 | 9 | |
| Q4 | 7 | 0.3125 |
| Q5 | 5 | 0.625 |
| Q6 | 4 | 1.25 |
| Q7 | 6 | 2.5 |
| Q8 | 13 | 5.0 |
| Q9 | 12 | 10 |
| Q10 | 14 | 20 |
| Q11 | 15 | 40 |
| Q12 | 1 | 80 |
| Q13 | 2 | 160 |
| Q14 | 3 | 320 |

The capacitor 146 is an optional element, which may be included in the circuit to further stabilize the clock frequency.

A selected output of the counter 142 (for example, $Q_{9-14}$ (pins 11, 14, 15, 1, 2, 3) may be wired to a flip-flop 148, which in the presently preferred embodiment is based upon a LIDS equivalent 4013 integrated circuit, LIDS LFF 4013. The output of the counter 142 is applied to the flip-flop 148 at pin 4 of the flip-flop, and serves to reset the flip flop 148. The flip flop 148 is set, however, by a differentiated pulse applied from a capacitor 150 in association with a series-wired resistor 152.

A resistor 154, resistor 156 and capacitor 158 control the switch 86 (whether that switch is momentary or of a toggle nature). Standby current is essentially zero due to the resistor 156 and the normal "0" state of pin 2 of the timer 148 (IC-6) for the off condition.

The above-described timer circuit provides a predetermined time frame during which the output of the timer circuit 38 is at ground ("0") potential. At the end of the time frame, the output level rises, a "1" condition. This output level, as should be apparent from FIG. 6, is then used to control the "on" time of the above-described pulse generator circuitry 40. After the unit has "timed out", however, the switch 140 must be turned off in order to get the timer circuit 38 ready for another cycle. This aspect of the operation of the timer circuit 38 limits the time in which an output of the pulse generator 40 may be applied to the electrodes 10, 12, and eliminates the chance of an accidental application. Various "on" times may advantageously be used, as a function of the frequency of the astable multivibrator 42, 44 and the output connections of the binary counter 60. For example, in one presently contemplated embodiment of the apparatus, available "on" times are approximately 180, 90, 45 and 22.5 seconds.

Referring now to FIGS. 2 and 3, there are seen mechanical aspects of apparatus 10 in according with the invention.

In FIG. 2, the support 24 for the electrodes 12 and 14 takes the form of a handle 160, which may be grasped by the user or a clinician, and used to maneuver and place the electrodes 12 and 14 on either side of the medial frenulum which is found beneath the upper lip. The frenulum is designated by the letter "F" in FIGS. 1 and 2. In the embodiment of the apparatus 10 shown in FIG. 2, an electrical cord or cable 162 extends to the handle 160, and serves to electrically connect the elecctrodes 12 and 14 to signal generating circuitry, not shown in that figure, located within a housing 164. The electrical cable 162 may be permanently affixed to the handle 160 and housing 164, but it may also be convenient to provide the cable 162 with removable jacks or plugs 166, to facilitate disassembly of the apparatus 10 for storage, service or replacement of parts.

Associated with the housing 164, which may conveniently be placed on a table or desk top, there may be a cradle 167 in which the handle 160 may rest when not in use.

Referring now to FIG. 3, another embodiment of the invention will now be described. In the embodiment illustrated in FIG. 3, the electrical components of the invention, including the signal generating means 26 and a portion of the power supply 28 are mounted within a handle-shaped housing 168, which may be grasped in the manner of the above-described handle 160. A lower portion of the housing 168 is shaped so as to mate with a receptable 170 in a base 172, so that when the base 172 rests on a table top or other supporting surface, the housing 168 may be fitted within the receptacle 170 and supported by the base 172 in the generally upright position shown in FIG. 3. Not shown in FIG. 3 is the above-described transformer, but it should be understood that the primary winding 32 of the transformer may advantageously be placed in the base 172, with a power supply cord 174 associated therewith. When so configured and arranged, placing of the housing 168 in the receptacle 170 of the base 172 causes the primary winding 32 of the transformer to excite the secondary winding 34, and to charge the power supply.

Externally of the housing 168, there may be provided a control 176, coupled to the potentiometer 84, to control the amplitude of the output.

The support structure 20, in the embodiment illustrated in FIG. 3, may be associated at its lower end with a jack 178, to facilitate removal of the support structure and its associated electrodes 12 and 14 from the housing 12. Similarly, the electrodes 12 and 14 themselves, may be coupled to the support structure 20 by jacks (not shown), thus facilitating replacement of the electrodes as desired.

It should be understood that the present invention may be embodied in other specific forms without departing from its spirit or essential attributes. Accordingly, reference should be made to the appended claims, rather than the foregoing specification, for an indication of the scope of the invention.

We claim:

1. A method for inhibiting nasal secretions, comprising the steps of placing in the oral cavity of the user on opposite sides of the frenulum and beneath the philtrum a pair of electrodes, and generating and applying to said electrodes a stimulating signal, wherein, said step of generating a stimulating signal is performed by generating a series of positive pulses having pulse widths of about one second, and spacing said pulses by about one second.

2. A method in accordance with claim 1, wherein said step of forming said pulses is so performed that said pulses have amplitudes which increase stepwise to a maximum.

3. A method in accordance with claim 2, wherein said step of generating a stimulating signal includes the further step of generating negative pulses during the intervals between said positive pulses, so that the net D.C. output per cycle is zero.

4. Apparatus for inhibiting nasal secretions by selective neural stimulation, comprising: a pair of means for placement beneath the upper lip of a user of the apparatus and adjacent to the philtrum; hand-holdable mounting means coupled to said electrode means for supporting said electrode means and spacing said electrodes relative to each other, the spacing of said electrode means being such as to facilitate placement of said electrode means at respective opposite side of the frenulum, and an electrical signal generator electrically coupled to said electrode means, said electrode means and portions of said mounting means being selectively placeable in the oral cavity of a user so as to apply a signal generated by said signal generator to the region of the oral cavity beneath the upper lip of a user adjacent to the philtrum and on opposite sides of the frenulum.

5. Apparatus in accordance with claim 4, and a housing having said signal generator disposed therein, said electrode means and said mounting means being operatively coupled to said housing, said housing comprising handle means for positioning said electrodes.

6. Apparatus in accordance with claim 5, and a base member complemental with said housing whereby said apparatus may be supported by said base member, a power supply in said housing for driving said signal generator, and means in said base member for selectively charging said power supply when said housing is received in said base member.

7. Apparatus in accordance with claim 4, wherein said signal generator comprises means for providing a signal which comprises a series of positive pulses of about one second in duration each made up of individual pulses of about 0.5 msec. duration, said positive pulses being spaced from each other by about one second.

8. Apparatus in accordance with claim 7, wherein said signal generator includes means for providing negative pulses during those intervals in which said positive pulses are off, whereby the net D.C. output per cycle is zero.

9. Apparatus in accordance with claim 8, wherein said positive pulses are ascending stepped pulses.

10. Apparatus in accordance with claim 8, and switch means associated with said housing and said signal generator for activating said signal generator and timer means responsive to said switch means, said timer means enabling said signal generator to produce an output for a predetermined period and then turning said signal generator off.

11. Apparatus in accordance with claim 7, wherein said signal generator comprises means for producing a series of positive pulses of ascending stepped waveform up to a maximum of about six volts, with a pulse width of about one second and a frequency of about 30 Hz.

12. Apparatus in accordance with claim 11, wherein said signal generator comprises means for producing negative pulses during those intervals in which said positive pulses are off, whereby the net D.C. output per cycle is zero.

13. Apparatus in accordance with claim 12, wherein said signal generator comprises multivibrator means and power amplifier means.

14. For use in apparatus for inhibiting nasal secretions by selective neural stimulation comprising a signal generator and electrode means for applying to a user a signal generated by said signal generator, said electrode means comprising: a spaced pair of electrodes shaped for placement beneath the upper lip of a user of the apparatus adjacent to the philtrum, mounting means coupled to said electrodes for supporting said electrodes and spacing said electrodes relative to each other, said mounting means comprising support members coupled to respective electrodes of said pair, means coupled to and interconnecting said support members to maintain said respective electrodes and said rod members in spaced relation with respect to each other, the spacing of said electrodes being such as to facilitate placement of said electrodes at respective opposite sides of the frenulum of a user, and electrical connector means operatively associated with said last-mentioned means for selectively electrically coupling said electrodes to a signal generator.

* * * * *